United States Patent [19]

Hofmann et al.

[11] Patent Number: 4,963,152
[45] Date of Patent: Oct. 16, 1990

[54] ASYMMETRIC PROSTHETIC TIBIAL COMPONENT

[75] Inventors: Aaron A. Hofmann, Salt Lake City, Utah; Joseph S. Skraba, Austin, Tex.

[73] Assignee: Intermedics Orthopedics, Inc., Austin, Tex.

[21] Appl. No.: 372,314

[22] Filed: Jul. 17, 1989

Related U.S. Application Data

[63] Continuation of Ser. No. 923,338, Oct. 27, 1986.

[51] Int. Cl.$^5$ .............................................. A61F 1/24
[52] U.S. Cl. ...................................... 623/18; 623/20; 623/39
[58] Field of Search ................... 623/16, 18, 20, 39

[56] References Cited

U.S. PATENT DOCUMENTS

| | | | |
|---|---|---|---|
| 4,055,862 | 11/1977 | Farling | 623/18 |
| 4,205,400 | 6/1980 | Shen et al. | 623/18 |
| 4,459,985 | 7/1984 | McKay et al. | 623/20 |
| 4,479,271 | 10/1984 | Bolesky et al. | 623/18 |

FOREIGN PATENT DOCUMENTS 2465470   4/1981   France .................................. 623/18

*Primary Examiner*—Robert A. Hafer
*Assistant Examiner*—Charles H. Sam
*Attorney, Agent, or Firm*—John R. Merkling

[57] ABSTRACT

A surgeon-assemblable asymmetric tibial prosthesis with a snap-in tibial insert for surface replacement of the proximal tibia. The tibial prosthesis, consisting of two parts, a baseplate and a right or left knee specific insert, is used in conjunction with prosthetic femoral and patellar components. Asymmetry is created by having the radius which describes the medial condyle slightly greater, preferably ⅛", than the radius describing the lateral surface. The baseplate exhibits symmetry about an anterior/posterior centerline, allowing it to be used on right or left proximal tibias by rotation of the component 180° about the centerline. The insert is contoured to provide an anatomically correct surface which articulates with the condyles of the femoral prosthesis. The anatomic fit contributes to normal range of motion since there is less chance of lateral overhang to cause soft tissue impingement. The increased cortical rim contact permits direct load transfer to the stronger cortical bone. In the preferred embodiment, two fully threaded bond screws secure the baseplate to the tibial bone surface and four pegs project from the inferior baseplate surface into the areas of the strongest tibial cancellous bone to provide torsional stability and reduce shear stress at fixation interfaces.

7 Claims, 4 Drawing Sheets

ASYMMETRIC PROSTHETIC TIBIAL COMPONENT

This is a continuation of co-pending application Ser. No. 06/923,338 filed on 10/27/86.

BACKGROUND OF THE INVENTION

This invention is in the general area of orthopedic prostheses, particularly tibial prostheses.

The tibia is situated at the front and inner side of the leg and, except for the femur, is the longest and largest bone in the skeleton. It is prismoid in form, expanded above, where it enters into the knee joint. The head of the tibia is large and expanded on each side into two eminences, the tuberosities. These present two smooth concave surfaces which articulate with the condyles of the femur. The medial condyle is more prominent anteriorly and broader both in the anterior-posterior and transverse diameters than the lateral condyle. Accordingly, the lateral articular surface of the tibia is longer, deeper and narrower than the medial surface of the tibia so as to articulate with the lateral condyle. The medial surface is broader and more circular, concave from side to side, to articulate with the medial condyle. The anterior surfaces of the tuberosities are continuous with one another, forming a single large surface which is somewhat flattened. Posteriorly the tuberosities are separated from each other by a shallow depression for attachment of ligaments. The inner tuberosity presents posteriorly a deep transverse groove for the insertion of a tendon.

In the past, manufacturers of tibial prostheses have ignored the anatomical differences between the medial and lateral condyle compartments. Most prostheses are constructed of a totally symmetric baseplate component for support and either a left or right knee-specific tibial insert or a surgeon-assembled neutral insert. Although the symmetrical components are interchangeable from the right to the left tibia, they invariably either overhang the lateral tibial bone or are undersized on the medial tibial bone surface.

The symmetrical prostheses generally feature center stems, either porous coated or smooth, or porous coated pegs. Further studies such as "An Evaluation of the Load Bearing Capability of the Cancellous Proximal Tibia with Special Interest in the Design of Knee Implants" by J. A. Johnson et al., 29th Annual ORS, Anaheim, CA, Mar. 8–10, page 403 (1983), show that the strongest portions of the tibia head are located at the lateral and medial portions of the tibia, with the weakest bone located in the central portion. The capacity of the bone to sustain load is important to the long-term survival of the reconstructed knee, and failure of the cancellous bone leads to subsidence of the implanted prosthesis. It would be difficult, if not impossible, to design a totally symmetrically tibial prosthesis with multiple pegs properly positioned since the pegs would either be too close to the outer wall of the bone or located too much towards the inner, soft portion of the bone, depending on whether the implant was on the right or left knee.

The prior prostheses have been designed to be totally symmetrical to minimize inventory costs. Unfortunately, the result is to compromise the fit of the prosthesis. Prior art prostheses have also usually been factory assembled. This is disadvantageous since either a large inventory of prostheses of various dimensions must be maintained or the surgeon must again settle for a less than optimal fit. Another disadvantage is that it is difficult to use bone screws to secure the baseplate of the factory assembled prosthesis.

It is therefore an object of the present invention to provide a tibial prosthesis which closely approximates the natural tibial anatomy.

It is a further object of the present invention to provide a tibial prosthesis with an anatomic fit contributing to the normal range of motion.

It is a still further object of the present invention to provide a tibial prosthesis wherein the long-term stability of the implant, both with respect to adhesion and subsidence, is optimized.

It is another object of the present invention to provide a tibial prosthesis which is extremely biocompatible and strong.

It is still another object of the present invention to provide a surgeon-assembled tibial prosthesis formed from modular components which can be used to provide the closest fit possible to the natural anatomic structure with the minimum inventory expense.

SUMMARY OF THE INVENTION

An asymmetric tibial prosthesis with a surgeon-assembled tibial insert for surface replacement of the proximal tibia, used in conjunction with prosthetic femoral and patellar components. The prosthesis is preferably assembled from two components: a knee specific tibial insert formed of a low friction, biocompatible material having a low wear rate, such as ultra-high molecular weight polyethylene (UHMWPe), and an asymmetric metal backed tibial baseplate. Assymmetry is created by having the radius which describes the medial condyle slightly greater than the radius describing the lateral condyle. However, the baseplate is symmetrical about the anterior/posterior centerline, allowing it to be used on either tibia without decreasing the anatomic fit by rotating the baseplate 180° about the centerline. Common to each part is the asymmetric top surface profile, a result of the medial condyle compartment being larger than the lateral compartment. This feature allows a better fit of the prosthetic component to the proximal tibial surface. The medial/lateral length and medial condyle anterior/posterior width of the tibial baseplates are designed to encompass the anatomical range. The top profile of the insert follows that of the baseplate. The insert is sized to provide a combined insert-baseplate thickness approximating normal anatomical ranges when measured from the low point of the lateral and medial condyle compartments to the inferior surface of the baseplate.

The preferred embodiment of the tibial prosthesis has other features in addition to the asymmetric profile which enhance the range of motion and long term stability of the device. Four smooth cylindrical pegs project perpendicularly downward from the inferior plate surface in positions that correspond to the strongest cancellous bone at the medial-anterior, medial-posterior, lateral-anterior and lateral-posterior positions. Between the medial and lateral pair of pegs are two countersunk holes on the anterior/posterior centerline which accept fully-threaded bone screws, preferably large diameter (6.5 mm) screws. The holes are countersunk to allow up to approximately 20° of screw angulation.

The central area of the baseplate component features symmetric anterior and posterior relief notches used for a component locking mechanism, when positioned anteriorly, and for relief of the posterior cruciate ligament (PCL), when positioned posteriorly.

The prosthesis is implanted by resecting the bone at an angle to match the slope of the articulating surface of the patient's natural tibia, selecting an appropriately sized baseplate and insert, and securing the baseplate to the underlying bone. The asymmetric insert is then locked into the baseplate by means of medial and lateral posterior "L"-shaped protrusion fitting under overhangs in the baseplate. A central anterior snap-lock is engaged into a notch on the baseplate with an inferiorly-directed force.

The modular asymmetric system provides the surgeon who assembles the tibial prosthesis in place with maximum flexibility in sizing the prosthesis to approximate the patient's normal tibial anatomy, has superior fixation due to the bone screws and baseplate pegs, and has lower inventory costs than factory assembled components.

DETAILED DESCRIPTION OF THE INVENTION

Figure 1:
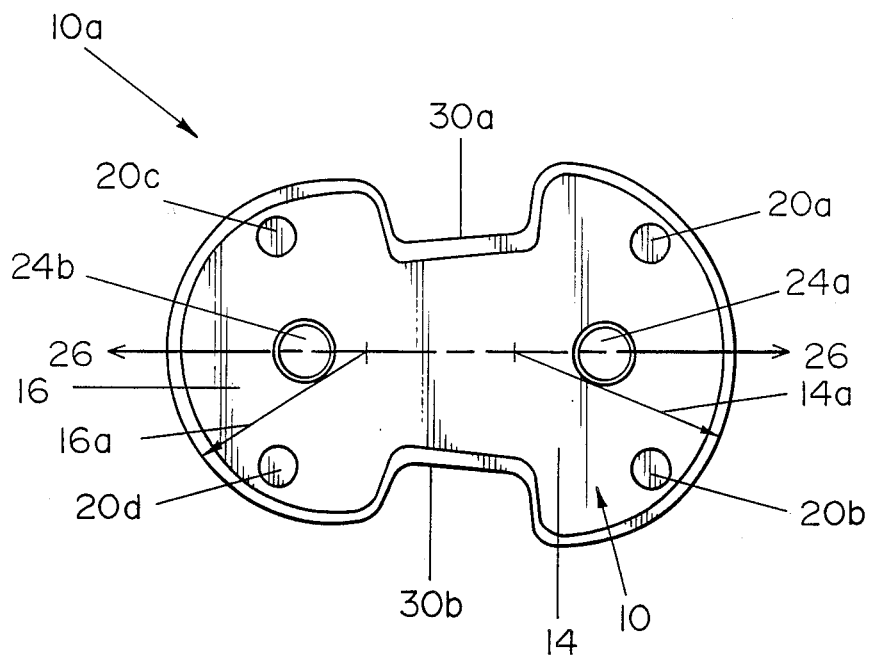
FIG. 1 is a plan view of the superior surface of the tibial baseplate according to the present invention.
Figure 2:
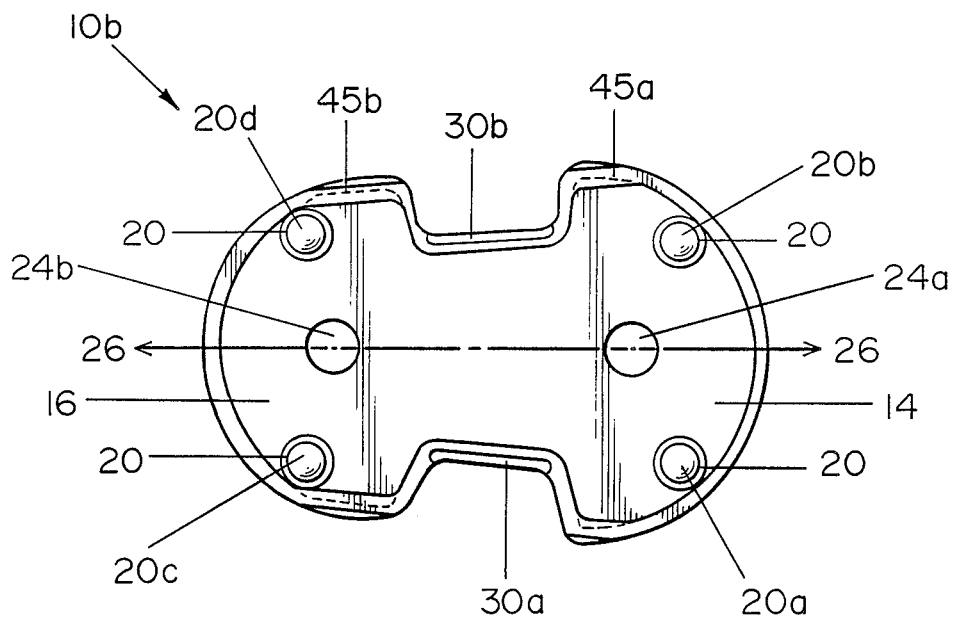
FIG. 2 is a plan view of the inferior surface of the tibial baseplate according to the present invention.
Figure 3:
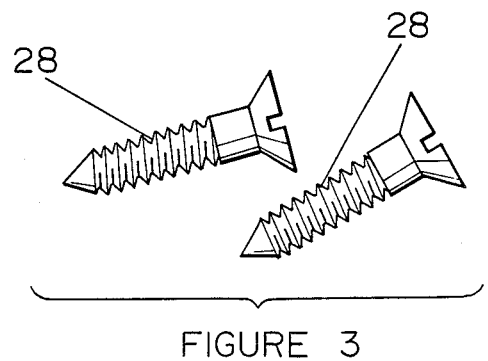
FIG. 3 is a plan view of fully-threaded cancellous bone screws for insertion into the tibial baseplate of the present invention.

The asymmetrical tibial prosthesis is preferably a two-piece, surgeon-assembled prosthesis used in the replacement of the tibial articulating surface and is intended to be used with femoral and patellar knee prosthesis components. A tibial prosthesis consisting of a single component having the same generally asymmetric anatomical outline and functionality could be constructed, although this is not preferred due to the superior fixation of a surgeon assembled prosthesis and higher inventory of the single component prosthesis required for optimum fit.

As shown in FIGS. 1 to 10, the preferred tibial assembly consists of two pieces: a tibial baseplate 10, preferably formed of a metal, and a tibial insert 12, preferably formed of a plastic. Common to each part is the asymmetric top surface profile, a result of the medial condyle compartment being larger than the lateral compartment. This feature allows a better fit of the prosthetic component to the proximal tibial surface.

The tibial baseplate 10 is designed to approximate the natural anatomic shape of the tibial head. In the preferred embodiment, the end 14 describing the medial condyle of the femur has a radius 14a approximately ⅛ inch greater than the radius 16a of the end 16 describing the lateral condyle. Projecting perpendicularly from the inferior plate surface 18 are four smooth cylindrical pegs 20, shown in FIGS. 2 and 4. The pegs 20 are located at medial-anterior 20a, medial-posterior 20b, lateral-anterior 20c and lateral-posterior 20d positions. Between the medial and lateral pair of pegs are two countersunk holes 24a, 24b on the anterior/posterior centerline 26, which accept fully-threaded bone screws 28. In the preferred design, large bore cancellous screws, approximately 6.5 mm, are used, FIG. 3. The preferred design of the counterbore allows approximately 20° of screw angulation, although it is possible to have up to 60° angle.

The use of a metal baseplate underlying a plastic insert reduces the maximum stress levels in both the insert and the trabecular bone. The baseplate in combination with at least one fixation post, i.e., bone screws or pegs, greatly reduces tension, compression and shear between the prosthesis and the trabecular bone.

Optional variations to the four smooth pegs include using as few as a single peg, porous coated pegs, smooth or porous pegs that are not perpendicular to the inferior surface, or large stems of rectangular, round or cruciate shape. Although multiple pegs are optimally positioned in the area of the strongest cancellous bone, it may be preferably at times to use a single central stem to secure the prosthesis.

The central area of the baseplate 10 features symmetric anterior 30a and posterior 30b relief notches. These notches 30a, 30b are interchangeable depending on whether the baseplate is replacing the right or left tibial surface. The anterior relief notch 30a is used in a component locking mechanism. The posterior relief notch 30b can provide relief for the posterior cruciate ligament (PCL), preferably retained during surgery.

Figure 4:
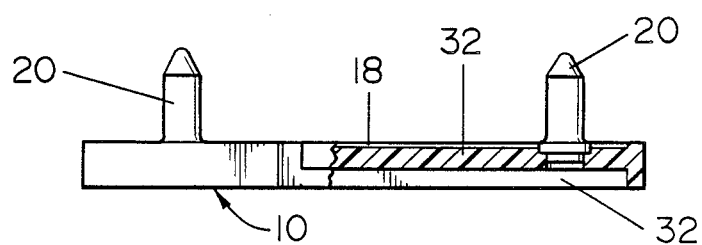
FIG. 4 is a plan view of the anterior of the tibial baseplate, partially in section.
Figure 5:
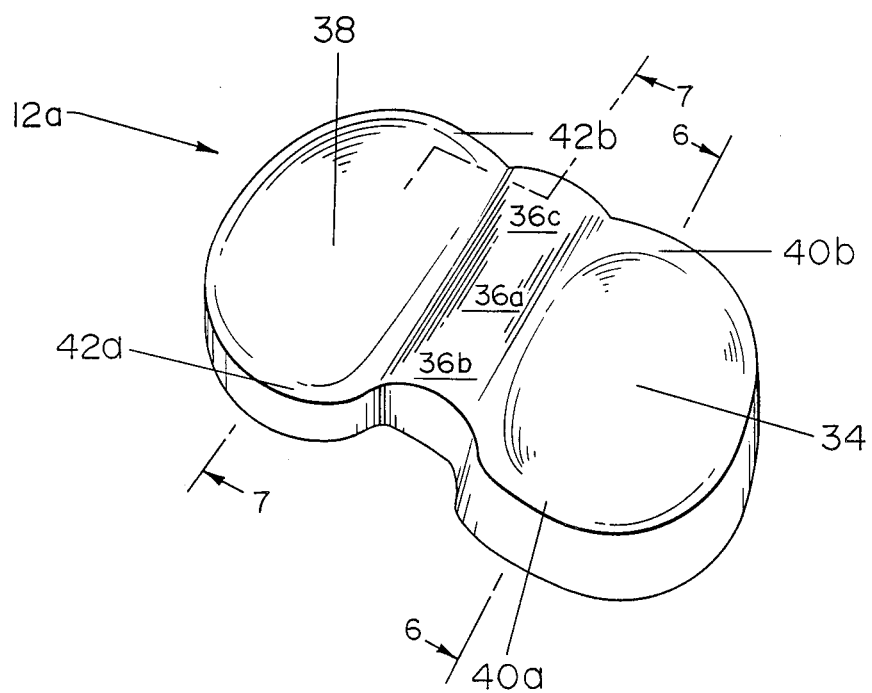
FIG. 5 is a perspective view of a tibial insert according to the present invention.
Figure 6:
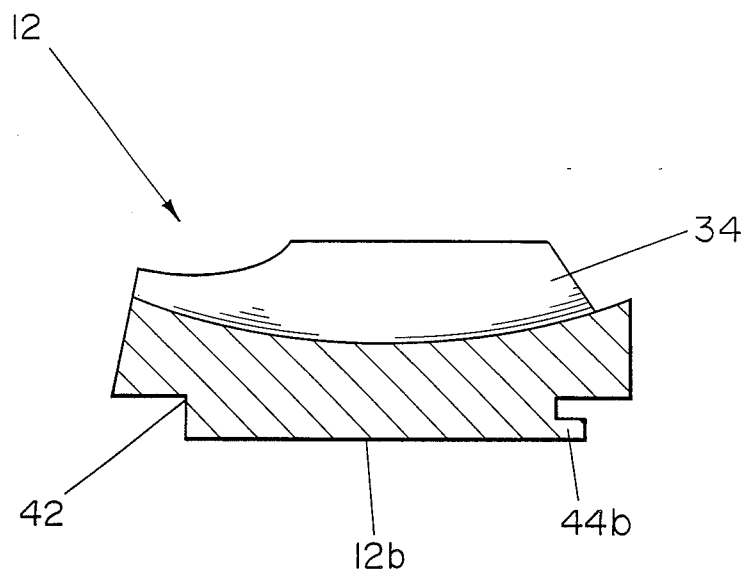
FIG. 6 is a plan view of the medial side of a left tibial insert according to the present invention.
Figure 7:
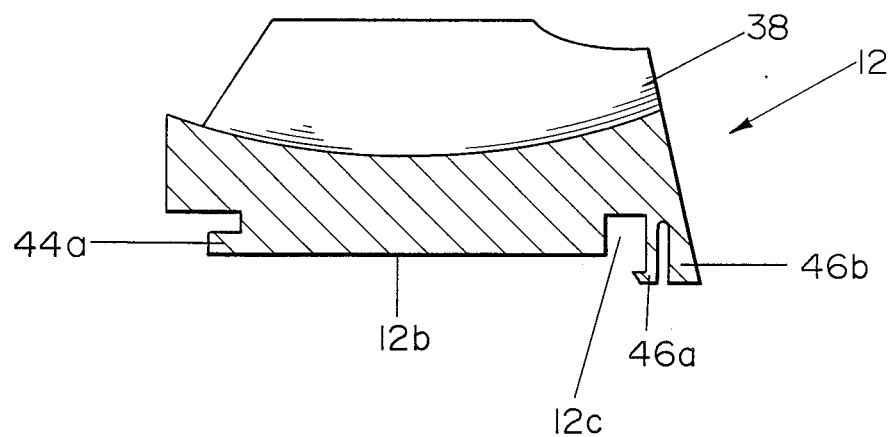
FIG. 7 is a plan view of the lateral side of a left tibial insert according to the present invention.
Figure 8:
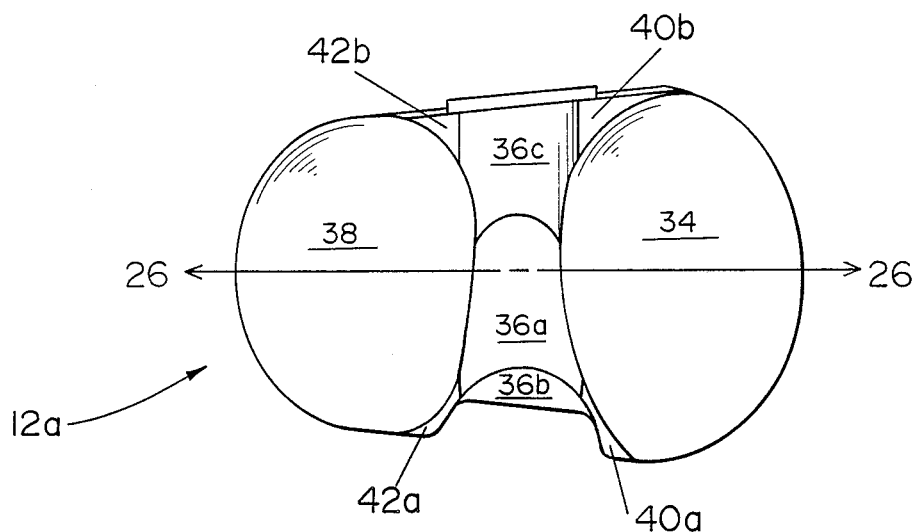
FIG. 8 is a plan view of the superior surface of a left tibial insert according to the present invention.
Figure 9:
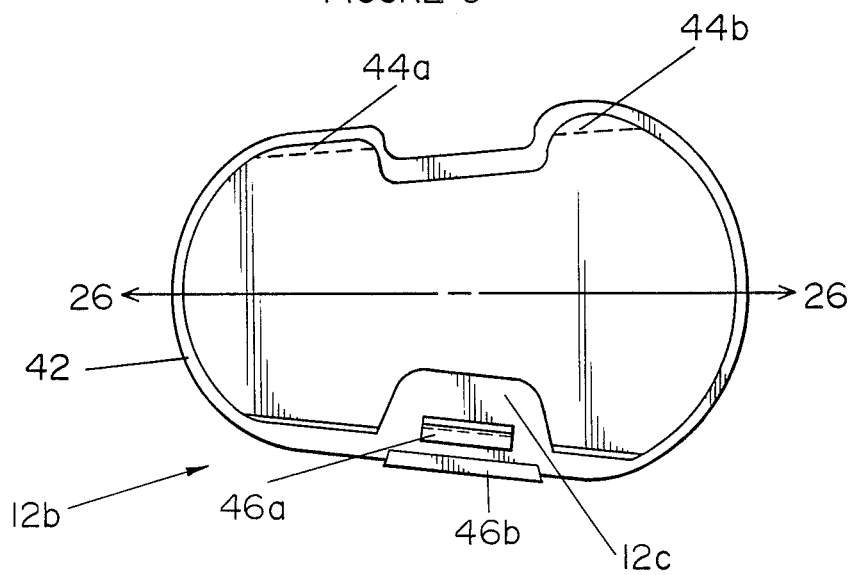
FIG. 9 is a plan view, partially in section, of the inferior surface of a left tibial according to the present invention.
Figure 10:
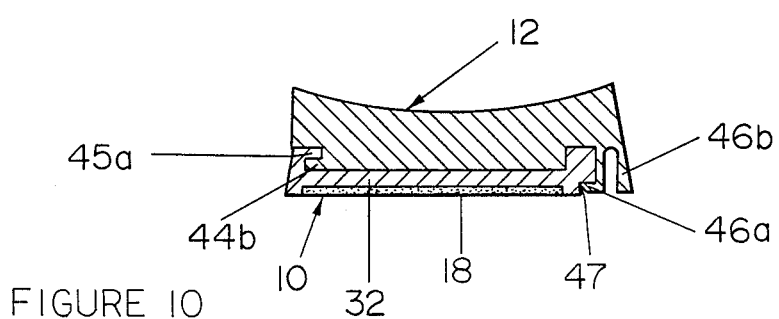
FIG. 10 is a cross-sectional view of a tibial insert secured within the baseplate according to the present invention.

In one construction, shown in FIG. 4, a porous layer 32 of commercially pure titanium is sintered to the interior plate surface 18, formed of a titanium alloy, such as Ti6A14V, using void metal technology. This material acts to increase the bone cement/implant interface strength, where appropriate, or, in non-cemented cases, presents a surface compatible for bone ingrowth. Other surface textures such as waffle patterns, grooves or pockets and other strong biocompatible materials such as stainless steel, cobalt-chrome, ceramic or plastic composites could also be used.

The superior insert surface 12a, shown in FIGS. 5-8, is divided into 3 areas; a medial condyle compartment 34, a tibial eminence 36, and a lateral condyle compartment 38. The two condylar compartment areas 34, 38 form the articulating surface for the femoral component. The medial condyle compartment 34 includes both an anterior 40a and a posterior 40b lip to limit anterior and posterior motion. The central antero-medial area of the medial condyle compartment 34 is shaped so as to not limit normal external rotation of the femoral-tibial couple. The lateral condyle compartment 38 is significantly flatter than the medial condyle compartment 34, with slight anterior 42a and posterior 42b lips. The central antero-lateral portion of the lateral condyle compartment 38 is also contoured, but to a lesser extent than the medial condyle compartment 34.

The insert 12 is preferably formed of an ultra-high molecular weight polyethylene (UHMWPe) in pure or fiber reinforced form produced by injection molding, compression molding or machining from bar or slab stock. Other biocompatible, low friction materials having a low wear rate, which can be shaped by molding or machining, could also be used.

The contouring of the condyle compartments allows normal internal and external rotation of the articulating couple. The central tibial eminence 36a supplies medial-lateral stability. The anterior third 36b of the eminence is relieved to allow the normal degree of hyperextension, approximately 5°. The posterior central area 36c of the insert 12 is notched to allow clearance for the PCL, as with the baseplate 10.

The contouring is designed to produce a knee-specific insert which, in combination with the underlying baseplate, presents a more natural anatomical surface to the femoral and patellar prostheses. The combination is intended to be implanted to provide an articular surface which is parallel to the axis of the natural articulating surface, in contrast to prior art prostheses presenting an articular surface at a fixed angle to the axis of the tibia. This is preferably achieved by matching the patient's posterior slope angle with a cutting jig and resecting a piece of bone. Next, a combined insert-baseplate thickness is selected which corresponds to the amount of bone resected, and the baseplate and insert are secured in place. The more anatomically correct reconstruction, having a slight tilt downwardly towards the posterior of the prosthesis, provides a more uniform weight-bearing surface. In an alternate embodiment, a prosthesis is constructed having an insert with a greater thickness anteriorly than posteriorly which provides a sloping surface when the bone is resected perpendicularly to the tibia.

As shown in FIGS. 6, 7, 9 and 10, the inferior insert surface 12b is flat, with an indented edge 42 around the outer periphery. The edge 42 allows the insert 12 to nest into the superior baseplate recess 10a. The asymmetric insert 12 is locked into the baseplate 10 by means of medial and lateral posterior "L" shaped protrusions 44a, 44b which fit under overhangs 45a, 45b in the baseplate 10. A central anterior snap-lock 46a, 46b is engaged into notch 30a on the baseplate 10 with an inferiorly-directed force. Both anterior notches 30a, 30b include a locking step 47 which secures the tibial insert 12 in place. Although present in both notches 30a, 30b, the locking step 47 is only used when the notch 30 is positioned anteriorly.

Tibial inserts 12 are designed specifically for right or left knees. For general inventory purposes, there are two sizes of inserts. These fit into any of four sizes of baseplates as measured by their medial/lateral length and medial condyle anterior/posterior width and range from 69 mm medial/lateral and 48 mm anterior/posterior in size one to 84 mm medial/lateral and 58 mm anterior/posterior in size four. The smaller insert fits into the recessed area of the smaller two sizes of the tibial baseplate and the larger insert fits into the recess of the larger two sizes of baseplate. The inserts are provided in five thicknesses to allow a combined insert-baseplate thickness of 7 mm to 16 mm, when measured from the low point of the medial and lateral compartments to the inferior surface of the baseplate. These sizes encompass the normal adolescent and adult anatomical ranges.

Variations of tibial inserts include a reversible neutral insert, different condylar geometries which allow more or less articulating constraint to compensate for soft tissue anomalies, or different assembly/locking arrangements.

This invention, an asymmetric tibial prosthesis, has been described with reference to specific embodiments. Modifications and variations will occur to those skilled in the art from the above detailed description. Such modifications and variations are intended to come within the scope of the appended claims.

We claim:

1. A tibial prosthesis comprising
   a base having
      a medial end with a first arcuate outer perimeter,
      a lateral end with a second arcuate outer perimeter, said first arcuate outer perimeter having a first radius of curvature greater than a second radius of curvature associated with the second arcuate outer perimeter,
      a first notch between the medial end and the lateral end, the first notch being in front of an anterior-posterior centerline, and
      a second notch between the medial end and the lateral end, the second notch being behind the anterior-posterior centerline, said ends being substantially symetric with respect to said anterior-posterior centerline and said first and second notches being arranged in mirror-image relationship across said centerline;
   means for securing said base to a resected surface on a patient's tibia; and
   an insert having a medial condyle compartment and a lateral condyle compartment for articulating with femoral condyles, said insert being secured to an upper surface of said base.

2. A tibial prosthesis according to claim 1, wherein the first radius of curvature is on the order of one eighth of an inch larger than the second radius of curvature.

3. A tibial prosthesis according to claim 2, wherein the insert comprises:
   an anterior edge and a posterior edge, the anterior edge being thicker than the posterior edge.

4. A tibial prosthesis according to claim 1, wherein the insert further comprises:
   a tibial eminence connecting the medial compartment and the lateral compartment.

5. A tibial prosthesis according to claim 1, wherein:
   the medial condyle compartment comprises a first curved surface of articulation for a femoral medial condyle, the first surface of articulation comprising:
   an anterior lip;
   a posterior lip; and
   a central depression;
   said first surface of articulation having a first surface radius of curvature and wherein;
   the lateral condyle compartment comprises a second curved surface of articulation for a femoral lateral condyle, the second surface of articulation comprising:
   an anterior lip;
   a posterior lip; and
   a central depression;
   said second surface of articulation having a second surface radius of curvature, said second surface of curvature being larger than said first surface radius of curvature.

6. A tibial prosthesis according to claim 5, wherein the first perimeter radius of curvature is on the order of one eighth of an inch larger than the second perimeter radius of curvature.

7. A tibial prosthesis according to claim 6, wherein the insert comprises:
an anterior edge and a posterior edge, the anterior edge being thicker than the posterior edge.

* * * * *